Figure 1:
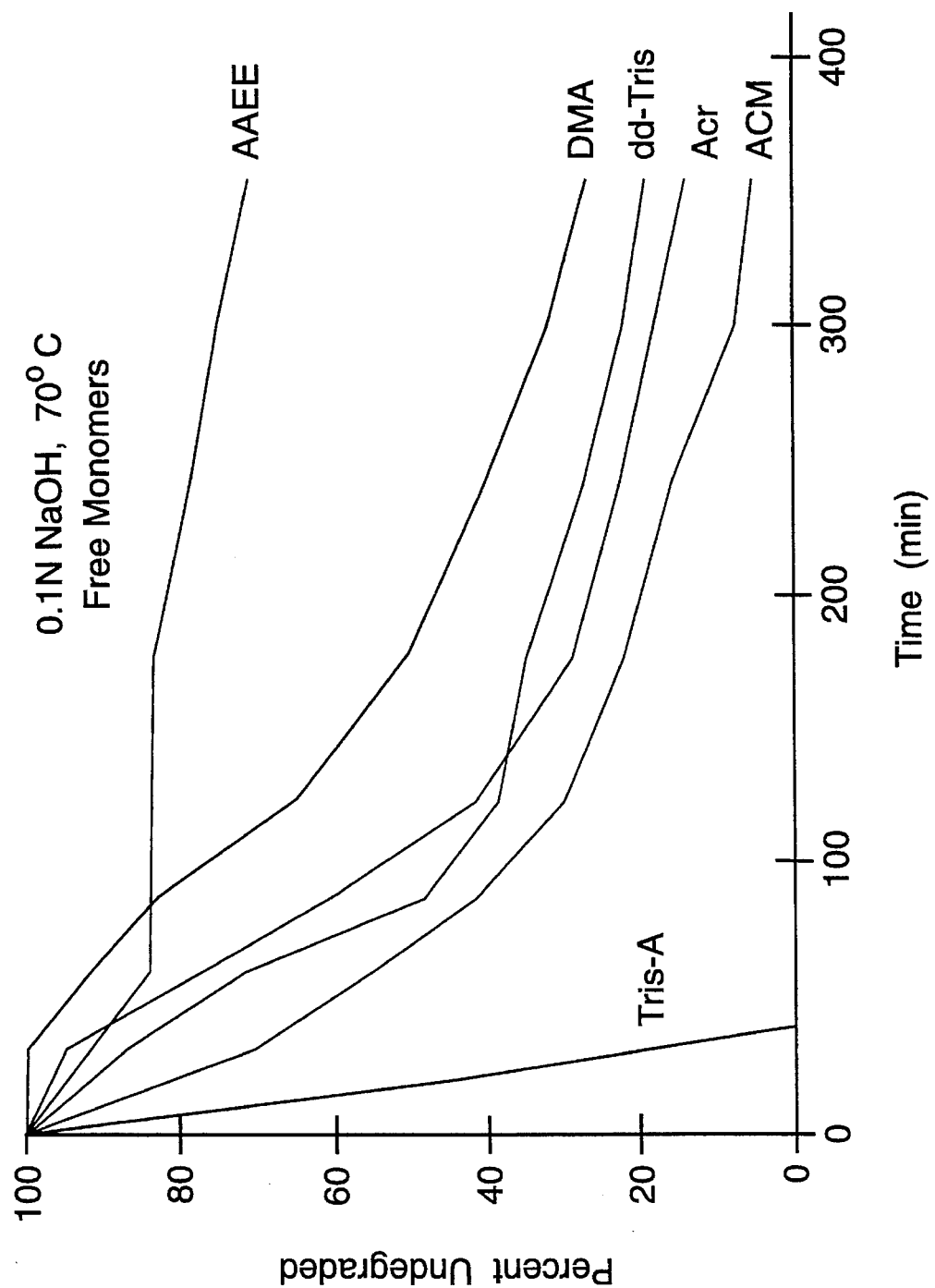

United States Patent [19]

Righetti et al.

[11] Patent Number: 5,470,916

[45] Date of Patent: Nov. 28, 1995

[54] FORMULATIONS FOR POLYACRYLAMIDE MATRICES IN ELECTROKINETIC AND CHROMATOGRAPHIC METHODOLOGIES

[76] Inventors: Pier G. Righetti, Via Archimede, 114, Milan I-20129; Marcella Chiari, Battista Brocchi, 11, Milan I-20131, both of Italy

[21] Appl. No.: 244,608

[22] PCT Filed: Aug. 5, 1992

[86] PCT No.: PCT/EP92/01772

§ 371 Date: Jun. 3, 1994

§ 102(e) Date: Jun. 3, 1994

[87] PCT Pub. No.: WO93/11174

PCT Pub. Date: Jun. 10, 1993

[30] Foreign Application Priority Data

Dec. 6, 1991 [IT] Italy .................................. M191A3271

[51] Int. Cl.⁶ .......................... C08F 120/58; C08F 2/00; C08F 2/46
[52] U.S. Cl. .......................... 525/296; 526/201; 526/304; 522/49; 522/63; 522/67
[58] Field of Search .................................. 526/304, 201; 522/49, 63, 67; 525/296

[56] References Cited

FOREIGN PATENT DOCUMENTS 0339678 11/1989 European Pat. Off. .
0367886 5/1990 European Pat. Off. .
48-017499 5/1973 Japan .
61-047741 3/1986 Japan .

*Primary Examiner*—Joseph L. Schofer
*Assistant Examiner*—Wu C. Cheng
*Attorney, Agent, or Firm*—Townsend and Townsend and Crew

[57] ABSTRACT

Matrices for electrokinetic and chromatographic separations, based on a unique class of mono- and disubstituted (on the amido nitrogen) acrylamides (e.g., acrylamido-N-ethoxy ethanol, acrylamido-N,N-diethoxy ethanol) offerthe following advantages: a) strong resistance to the alkaline hydrolysis (most zone separations occurring at basic pH values); b) a high hydrophilicity; and c) greater porosity, due to the larger $M_r$ value of the monomers. Such matrices can be prepared as 'chemically crosslinked' gels or as 'physical' gels, the latter consisting of strings of monofunctional monomer in the absence of crosslinker, at concentrations above the entanglement threshold. It is moreover possible to further increment the gel porosity by polymerizing it in the presence of laterally aggregating agents (e.g., polyethylene glycol of $M_r$ 6–20,000 Da), thus obtaining matrices which allow better resolution of large $M_r$ proteins and of nucleic acid fragments; by polymerizing the matrix in the presence of a gradient of the laterally aggregating agent, it is possible to obtain a porosity gradient even at a constant percent of monomers in the gel. Finally, photopolymerization (e.g., with methylene blue and a redox couple, sodium toluene sulfonate and diphenyliodonium chloride and light), instead with the standard red/ox catalysts, prevents formation of N-oxides of amines present in the polymerizing solution.

15 Claims, 9 Drawing Sheets

FORMULATIONS FOR POLYACRYLAMIDE MATRICES IN ELECTROKINETIC AND CHROMATOGRAPHIC METHODOLOGIES

The present invention refers to new polyacrylamide matrices possessing the following unique characteristics:
  a) very high resistance to alkaline hydrolysis;
  b) high hydrophilicity, so as to avoid hydrophobic interaction with macromolecules;
  c) higher porosity (either due to the use of monomers of larger molecular mass, or due to the use of laterally aggregating agents in the polymerization step);
  d) lack of oxidizing properties, typical of matrices polymerized with the standard redox couple (persulfate and N,N,N',N'-tetramethylethylene diamine, TEMED).

BACKGROUND OF THE INVENTION

Matrices exhibiting the above characteristics are obtained, according to the present invention, via the polymerization or co-polymerization of a unique class of N-mono- or di-substituted acrylamide monomers, by using methods which also belong to the present invention. Included in the present invention are also matrices obtained with mixtures of such polymers or co-polymers of the afore-mentioned acrylamides, or with mixtures of such polymers and co-polymers with agarose, dextrans or other hydrophilic polymers.

Polyacrylamide matrices, for separation in zone electrophoresis, were introduced already in 1959 by Raymond and Weintraub (Science, 130, 1959, 711–712) and further promoted for use in disc electrophoresis by Davis (Ann. N. Y. Acad. Sci. 121, 1964, 404–427), Ornstein (Ann. N. Y. Acad. Sci. 121, 1964, 321–349) and Hjertén (J. Chromatogr. 11, 1963, 66–70). Their popularity as electrophoretic supports stems from some fundamental properties, such as: a) optical transparency, including the ultraviolet; b) electrical neutrality, due to the absence of charged groups; c) possibility of synthesizing gels in a wide interval of porosities. During the years, the couple of monomers which has attained the greatest popularity has been acrylamide coupled to a cross-linker, N,N'-methylene bisacrylamide (P. G. Righetti, J. Biochem. Biophys. Methods 19, 1989, 1–20). However, several defects of such a matrix have been noticed upon prolonged use. The most dramatic drawback is its instability at alkaline pH values: after an electrophoretic run (most electrokinetic separations occur at alkaline pHs for both proteins and nucleic acids), the dangling amido bonds are partly hydrolyzed, originating carboxylic groups, which stay covalently bound to the polymer, which is thus transformed into a polyacrylate. This phenomenon generates strong electroendo-osmosis, with matrix swelling and considerable distortions. In practice, after only a single electrophoretic run, the polyacrylamide matrix cannot be re-used. This strongly limits its use in large-scale projects, such as the sequencing of the human genome, where the availability of re-usable matrices would greatly shorten the analysis time and allow for a quick progress of such a project around the world. Stable matrices would be also quite useful in capillary zone electrophoresis (CZE), where the gel cannot be extruded from the capillary when partially hydrolyzed or malfunctioning.

Another common problem is the limited range of molecular sizes which can be efficiently sieved by polyacrylamides. Such porosity range encompasses pore sizes from a few (2–3 nm) to ca. 20–30 nm in highly diluted matrices. This limits the use of polyacrylamides to protein separations, whereas agarose gels are today almost exclusively used for separation of nucleic acid fragments. Highly porous polyacrylamide matrices would thus allow fractionation also of nucleic acids in some intervals of length.

A third problem is linked to the use of the standard redox couple of catalysts: persulfate and TEMED. Since this is a redox couple, it is thus able to oxidize many substances containing amino groups (from primary to tertiary), thus producing N-oxides. Such N-oxides, which remain in the gel even after discharging excess of persulfate to the anode, are able to oxidize proteins, especially the —SH residues, to disulfide bonds (—S—S—).

Some earlier patent applications have addressed some of the problems described above and have proposed different types of monomers. In one instance (Kozulic, B. and Mosbach, K., Patent No. PCT/EP88/00515, Jun. 10, 1988) Trisacryl [N-acryloyl-tris(hydromethyl)aminomethane, NAT] has been advocated for producing hydrophilic, large pore gels for electrophoresis. The Trysacryl monomer had in fact been proposed for chromatographic support media (Girot, P. and Boschetti, E., J. Chromatogr. 213, 1981, 389–396). As it will be shown below, this monomer, while strongly hydrophilic, suffers from its inherent instability, as it degrades with zero-order kinetics. Its use for, e.g., reusable or long term storage matrices cannot be clearly advocated. In another patent application (Kozulic, B., European Patent No. 88810717.4 of Oct. 19, 1988) acrylamide-sugars have been proposed, such as N-acryloyl (or metacryloyl)-1-amino-1-deoxy-D-glucitol or the corresponding D-xylitol derivative. This class of acrylamido monomers, which certainly possess good hydrophilicity and a larger molecular mass than unsubstituted acrylamide, is also extremely unstable, as it degrades with zero-order kinetics and thus does not seem to be a valid alternative, just as poly(NAT) mentioned above. In another application (Shorr, R. and Jain, T., European Patent No. 89107791.9, Apr. 28, 1989) a broad class of N-mono- and di-substituted acrylamido monomers has been proposed as electrophoretic support media, including some of the monomers mentioned above. However, out of this vast class of potential monomers, Shorr and Jain have enucleated (and commercialized) only two preferred mixtures, as follows (verbatim quotation): "in one preferred embodiment, the polymers are formed by cross-linking polymerization of N,N-dimethylacrylamide with ethyleneglycol methacrylate. In another preferred embodiment, the polymers are formed by cross-linking polymerization of N,N-dimethylacrylamide and hydroxyethyl-methacrylate with N,N-dimethylacylamide". Also these formulations do not appear to be optimal. As it will be shown below, N,N-dimethylacylamide, and similar alkyl-substituted acrylamides, are too hydrophobic, while the various methacrylate cross-linkers are too prone to hydrolysis and hydrophobic as well. As a result of this, the commercialized product containing these formulations (Hydrolink) has to contain detergents to help in solubilizing the monomers. The corresponding emulsion often flocculates. These examples show that the problems formulated above, namely the design of new matrices possessing simultaneously a high hydrophilicity, a high resistance to hyrolysis and a larger pore size have not been addressed properly and are very far from being solved.

DESCRIPTION OF THE INVENTION

The present invention proposes new formulations able to eliminate such inconveniences, with vastly superior results in electrokinetic separations. Such formulations are obtained via polymerization or co-polymerization of a unique class of monomers having the following formula (I):

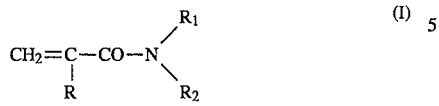

in which R represents hydrogen or $CH_3$, while $R_1$ and $R_2$, independently, represent hydrogen or a group of the formula $-[(CH_2)_n-O-(CH_2)_n-O-]_N H$, wherein n=2 or 3 and N=1–5, preferably 1, with the proviso that one of $R_1$ and $R_2$ is different from hydrogen. The preferred monomers of formula (I) are: N-(2-hydroethoxy)ethylacrylamide (=N-acryloylaminoethoxy ethanol) or the N-disubstituted derivative or the corresponding methacrylamido-derivatives, whose polymers and co-polymers (e.g., with N,N-dimethylacrylamide) exhibit good hydrophilicity, extreme resistance to hydrolysis and greater porosity than conventional polyacrylamides. Such characteristics can be found also in mixed-bed matrices, such as agarose/polyacrylamide, the latter obtained with the afore-mentioned monomers.

The present invention encompasses also procedures for obtaining gels (by polymerization or co-polymerization) via redox or preferably photocatalysis, but in the presence of laterally-aggregating agents (such as polyethylene glycols) for producing highly porous matrices, able to resolve high $M_r$ proteins and nucleic acid fragments. If, in the latter procedure, polymerization (or co-polymerization) is performed in the presence of a gradient of a laterally-aggregating agent, it is possible to obtain a porosity gradient even in presence of constant amounts of monomers in the gel. The above monomers can also be photopolymerized (or photo co-polymerized) e.g. with riboflavin and light, but preferably with methylene blue (generally in the presence of sodium toluenesulfinate and diphenyliodonium chloride), thus forming matrices free of N-oxides, unable therefore to oxidize proteins, as discussed above. The invention includes also the use of the monomers of the above formula (I) for preparing gel slabs for prolonged storage to be used in all electrokinetic methodologies for industrial, research and analytical uses and in the form of granulated material (either alone or as a surface coating of plastic or glass beads, or in combination with agarose and other hydrophilic polymers) as chromatographic support media. The advantages of matrices according to the present invention are discussed and illustrated below. Polyacrylamide matrices based on a novel class of N-mono- and di-substituted acrylamide monomer.

The example in FIG. 1 shows the hydrolysis kinetics of conventional acrylamide as compared with conventional N-mono- and di-substituted acrylamides and with the novel class of monomers according to the present invention. The free monomers, dissolved in 0.1N NaOH, are incubated at 70° C. for the times indicated, neutralized and then analyzed by capillary zone electrophoresis using mandelic acid as an internal standard. Peak integration has been obtained with the Beckman system Gold. It can be appreciated how the highly hydrophilic monomers reported by Kozulic (acrylamido sugars) and by Kozulic and Mosbach (NAT or Trisacryl) all exhibit degradation kinetics of the zero order, suggesting an intrinsic instability of such molecules. The various N-mono- and di-substituted acrylamides of the conventional type all display first order degradation kinetics, not vary dissimilar in shape from acrylamide. On the contrary, the monomers reported in the present invention [such as AAEE, N-(2-hydroethoxy)ethylacrylamide] reveal a unique behaviour of extreme hydrolytic stability.

Figure 2:
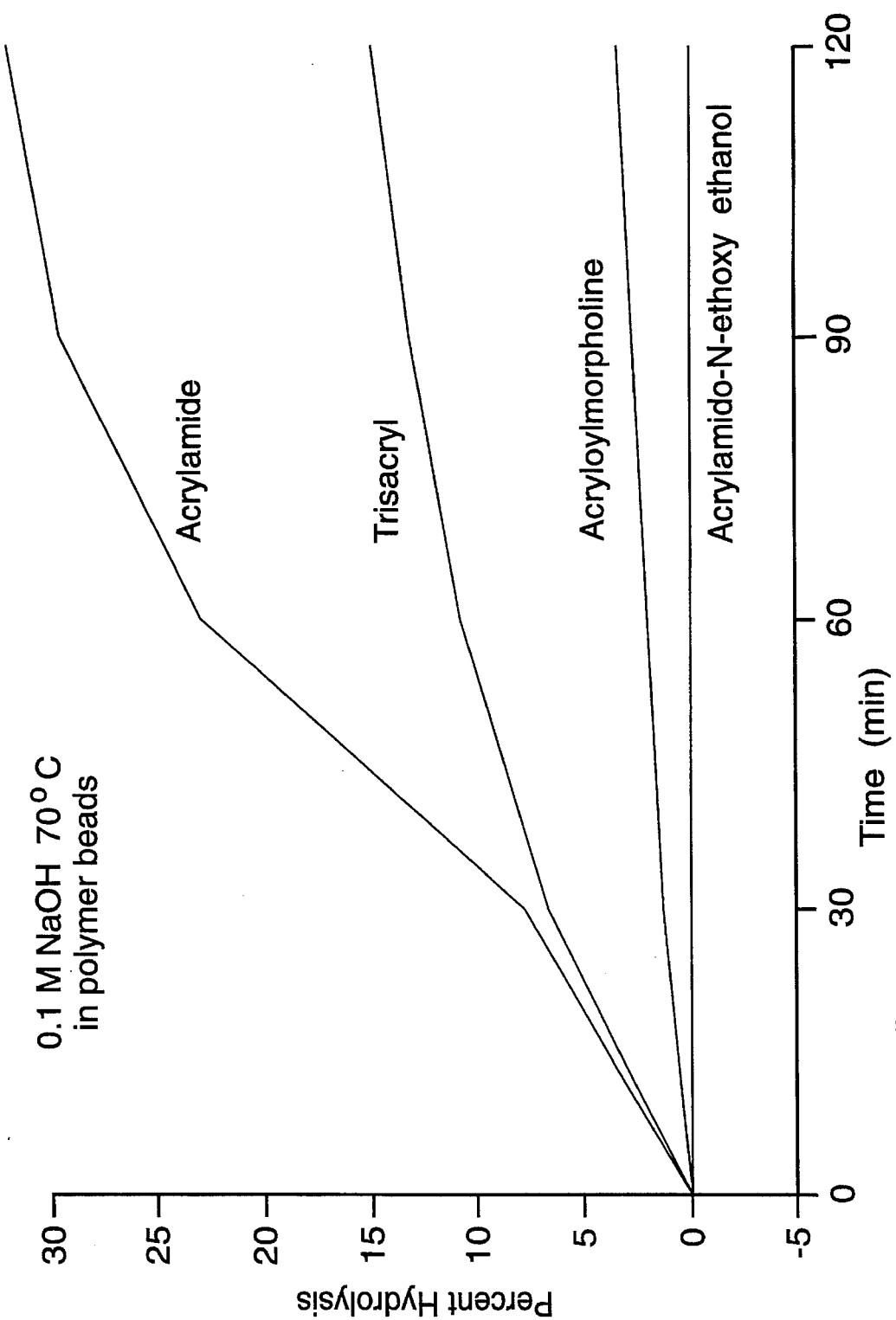

The difference in stability is much more emphasized when the monomers, instead of being free in solution, are engaged in the polymer matrix. In FIG. 2, the stability of conventional N-substituted acrylamides is again compared, but this time in the polymer reticulum. In this experiment, all polyacrylamides have been synthesized as spheres (by emulsion polymerization), which have then been hydrolyzed in 0.1N NaOH at 70° C. for the times indicated in FIG. 2. The assessment of the extent of hydrolysis in the polymer has been performed by frontal analysis, by titration of the free carboxyls obtained upon hydrolysis of the amide bond. It is seen how, in conventional polyacrylamide, at least 30% monomer has been hydrolyzed in only 2 hours of incubation. Conversely, in poly(AAEE) there is no evidence of hydrolysis in the same period whereas all other matrices, made of conventional N-substituted acrylamides, hydrolyse to different extents. (For a detailed discussion of this and the other Figures see hereinafter, in the section under the heading "Legends").

Figure 3:
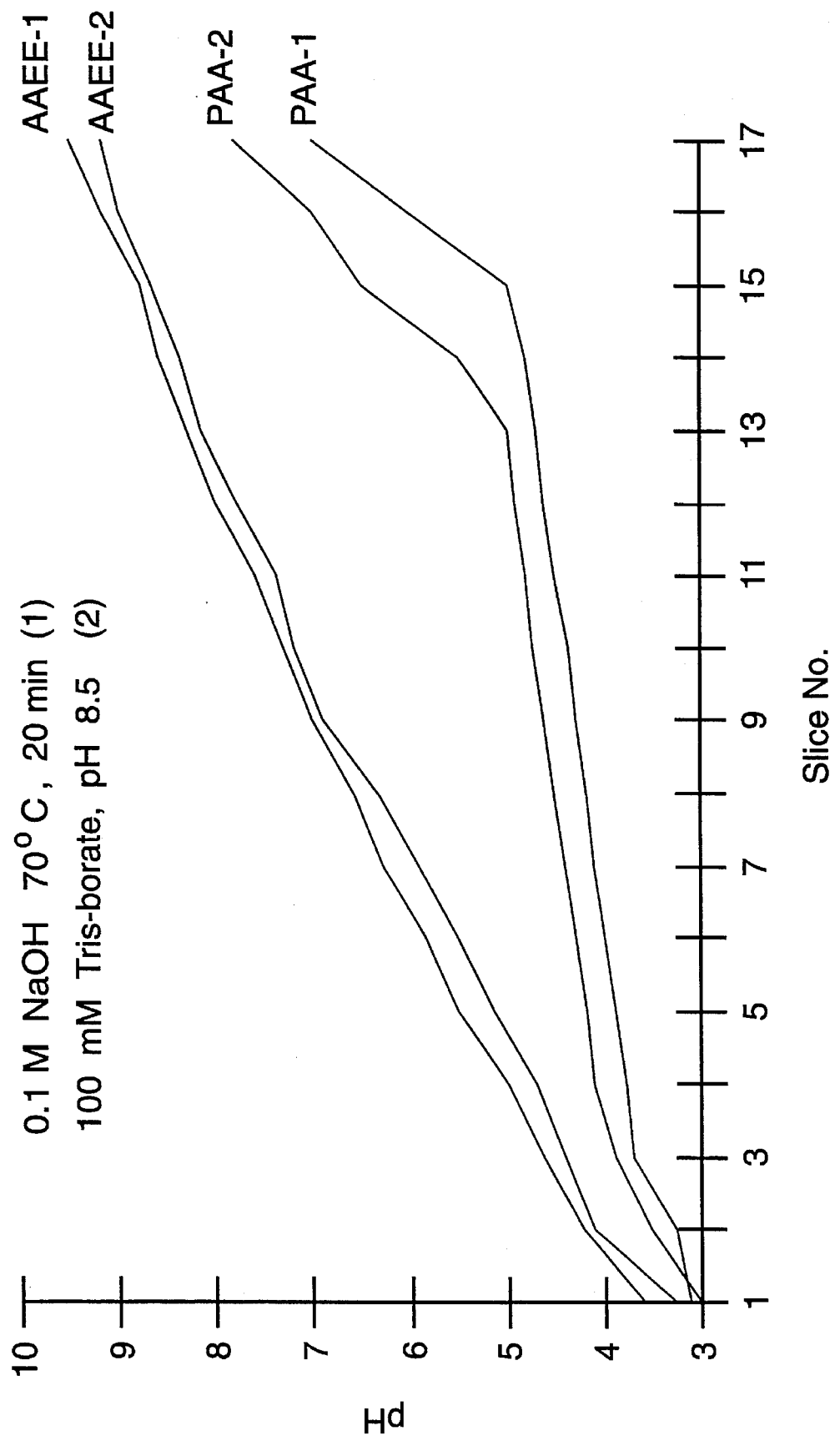

In the example of FIG. 3, the resistance to hydrolysis of the novel class of N-substituted acrylamides is shown in an isoelectric focusing experiment. Two slabs, one of poly(acrylamide) the other of poly(AAEE) are prepared and incubated either in 0.1N NaOH at 70° C. for 20 min (tracings 1) or overnight in 100 mM Tris-borate buffer, pH 8.5 (a typical buffer for DNA analysis, tracings 2). After washing in distilled water to eliminate excess NaOH or Tris-borated, the gels are desiccated and reswollen in 2% Ampholine pH 3–10. After isoelectric focusing, the pH gradient is measured by cutting gel slices (at 5 mm intervals) between anode and cathode. It is seen that in poly(AAEE) the pH gradient extends in a regular fashion in the expected interval (pH 3–10) whereas in poly(acrylamide) the pH gradient has completely acidified, even upon very mild hydrolytic conditions, such as overnight incubation in the presence of common buffers for zone electrophoresis. This last phenomenon is a clear indication of the presence of a large number of carboxyls in the matrix, which strongly acidify the pH gradient and generate a substantial elecroendo-osmotic flow (P. G. Righetti, J. Biochem. Biophys. Methods 19, 1989, 1–20). Similar results are obtained in gels containing immobilized pH-gradients.

Figure 4:
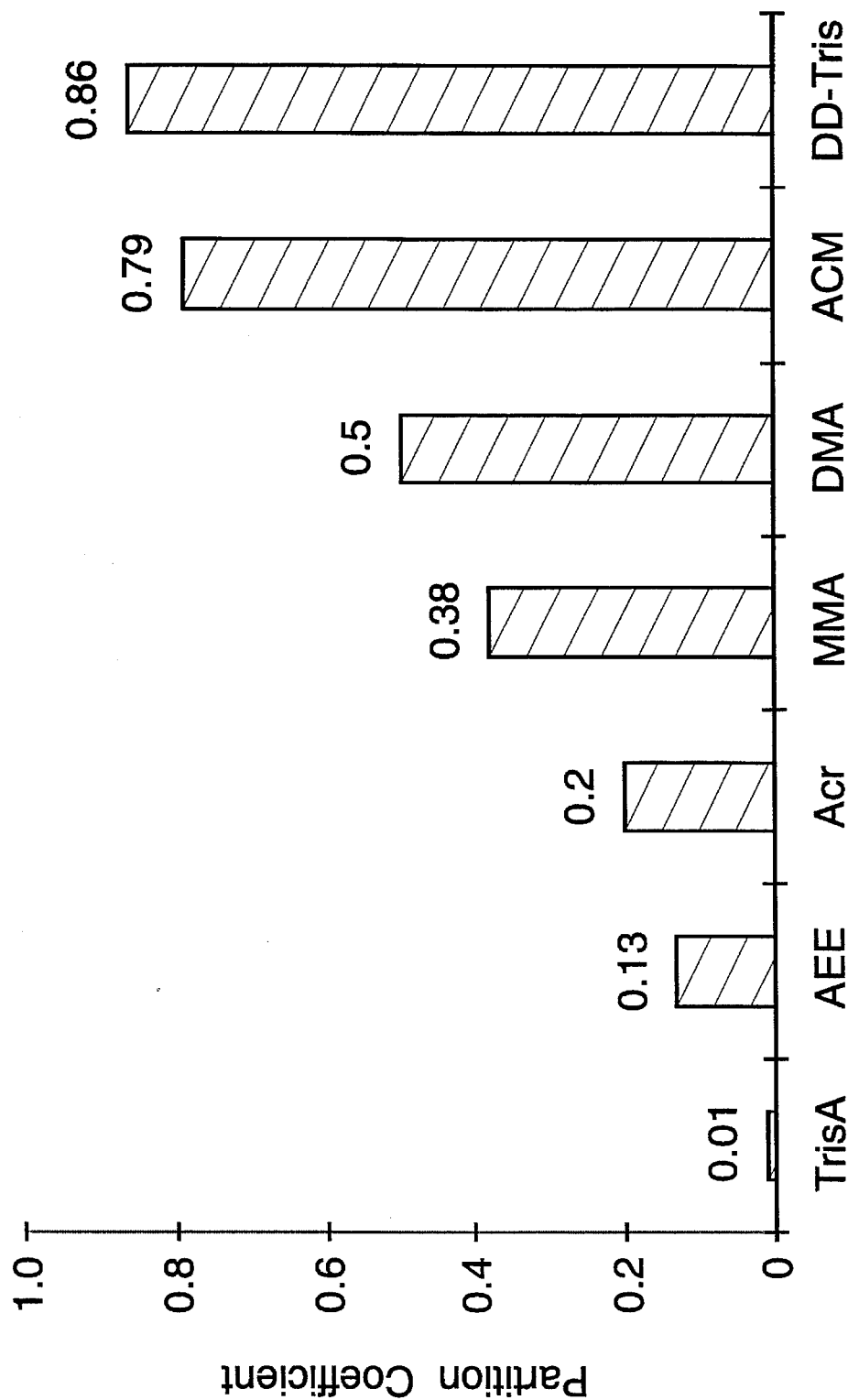

For demonstrating the hydrophilicity of our novel class of N-substituted monomers, aqueous solutions have been subjected to partitioning in n-octanol. Upon equilibration, the aqueous phase is analyzed by capillary zone electrophoresis (CZE) and the molar ratio in the two phases thus determined. FIG. 4 shows the partition coefficients of acrylamide, of its conventional N-substituted derivatives and of the novel monomers in the present invention: it is seen that trisacryl, as well as in general acrylamido sugars, are extremely hydrophilic (but also extremely prone to hydrolysis), whereas all other conventional N-substituted acrylamides are decidedly more hydrophobic than acrylamide. The novel monomers here reported (as exemplified by AAEE) are unique in that they display a markedly reduced partition coefficient (P=0.13), thus a more pronounced hydrophilicity as compared with acrylamide, while exhibiting a unique resistance to hydrolytic processes (see FIGS. 1–3). The maximum P value for obtaining hydrophilic gels is P=0.4: above such a value, the polymer, e.g. a poly(DMA), exhibits hydrophobic interaction with proteins. Above a P=0.8, the polymer cannot reswell any longer in protic solvents.

Such matrices resistant to alkaline hydrolysis are also extremely useful for coating the inner wall (usually of fused silica) of capillaries in CZE for eliminating the electroendo-osmotic flow (EEO). Suppression of EEO is fundamental in techniques such as isoelectric focusing, in which the pH gradient would be immediately destroyed by the fixed charges on the capillary wall, and for protein and peptide separations, since there is normally a strong adsorption of these polymers to the negatively charged capillary walls. One of the standard methods adopted for coating the capillary has been proposed by Hjertén (J. Chromatogr. 347, 1985, 191–198): the capillary is treated with a bifunctional agent (e.g., Bind Silane, 3-methacryloxypropyltrimethoxy silane) and then coated with 'strings' of polyacrylamide, in the absence of cross-linker. Long linear 'strings' are thus formed, which are covalently bound to the wall and quench the EEO flux. However, such a coating is extremely sensitive to alkaline conditions: if the capillary is used for isoelectric focusing, the EEO flux already manifests itself after only 5 runs. If, however, the capillary, pre-treated in the same way, is coated with linear chains of poly(AAEE) the EEO flux is still not appreciable after 50 runs. The bond between the fused silica wall and the bifunctional agent (Bind Silane) (of the type —Si—O—Si—) also contributes to the instability of the coating. An alternative is to use the method of Cobb et al., (K. A. Cobb, V. Dolnik and M. Novotny, Anal. Chem. 62, 1990, 2478–2483), which utilizes Grignard reagents for generating a direct —Si—C≡ bond between the silica wall and the bifunctional agent. By using this alternate method, and by coating the wall with linear chains of poly(acrylamide), the coating stability increases from 5 to only 10 runs. However, when using the Cobb method, coupled to linear chains of poly(AAEE), the EEO flux is still not evident after as many as 100 runs (Table I).

TABLE I

Influence of the type of capillary coating on the EEO* flux

| Type of cross-linker | Type of chain polymer | No. of electrophoretic runs |
| --- | --- | --- |
| —Si—O—Si— | poly(acrylamide) | 5 |
| —Si—O—Si— | poly(N-(2-hydroxyethoxy) ethylacrylamide) | >50 |
| —Si—C≡ | poly(acrylamide) | 10 |
| —Si—C≡ | poly(N-(2-hydroxyethoxy) ethylacrylamide) | >100 |

Figure 5:
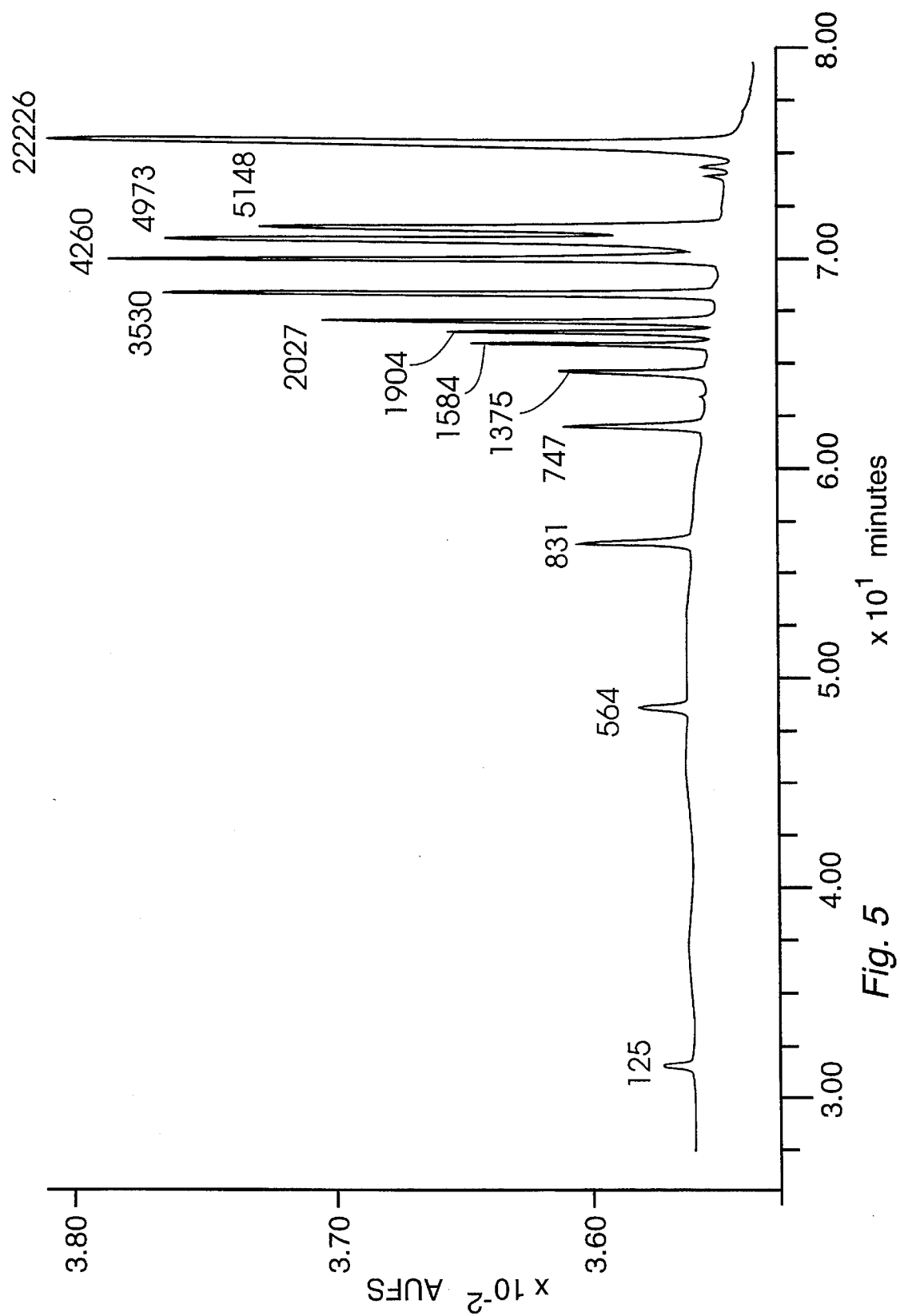

Matrices made of poly(AAEE) can be used not only for coating, but also as filling polymers in CZE, both as chemically cross-linked as well as uncross-linked polymers. A unique application is their use as viscous solutions, i.e. as liquid, linear, un-crosslinked polymers at concentrations above the entanglement threshold. Such fillings are very useful in CZE, since the polymer network is not distorted in the high electric fields and no air bubbles are formed, which usually disrupt the electric circuit in CZE. FIG. 5 gives an example of a separation of DNA fragments, ranging in size from 125 base pairs (bp) up to 22,226 bp in a 10% viscous (un-crosslinked) poly(AAEE) solution: the electropherogram shows full resolution of all 13 fragments contained in the mixture, a separation which cannot be achieved even in standard agarose gels, where the 5.1 and 4.9 kbp fragments co-migrate in a single zone.

Figure 6:
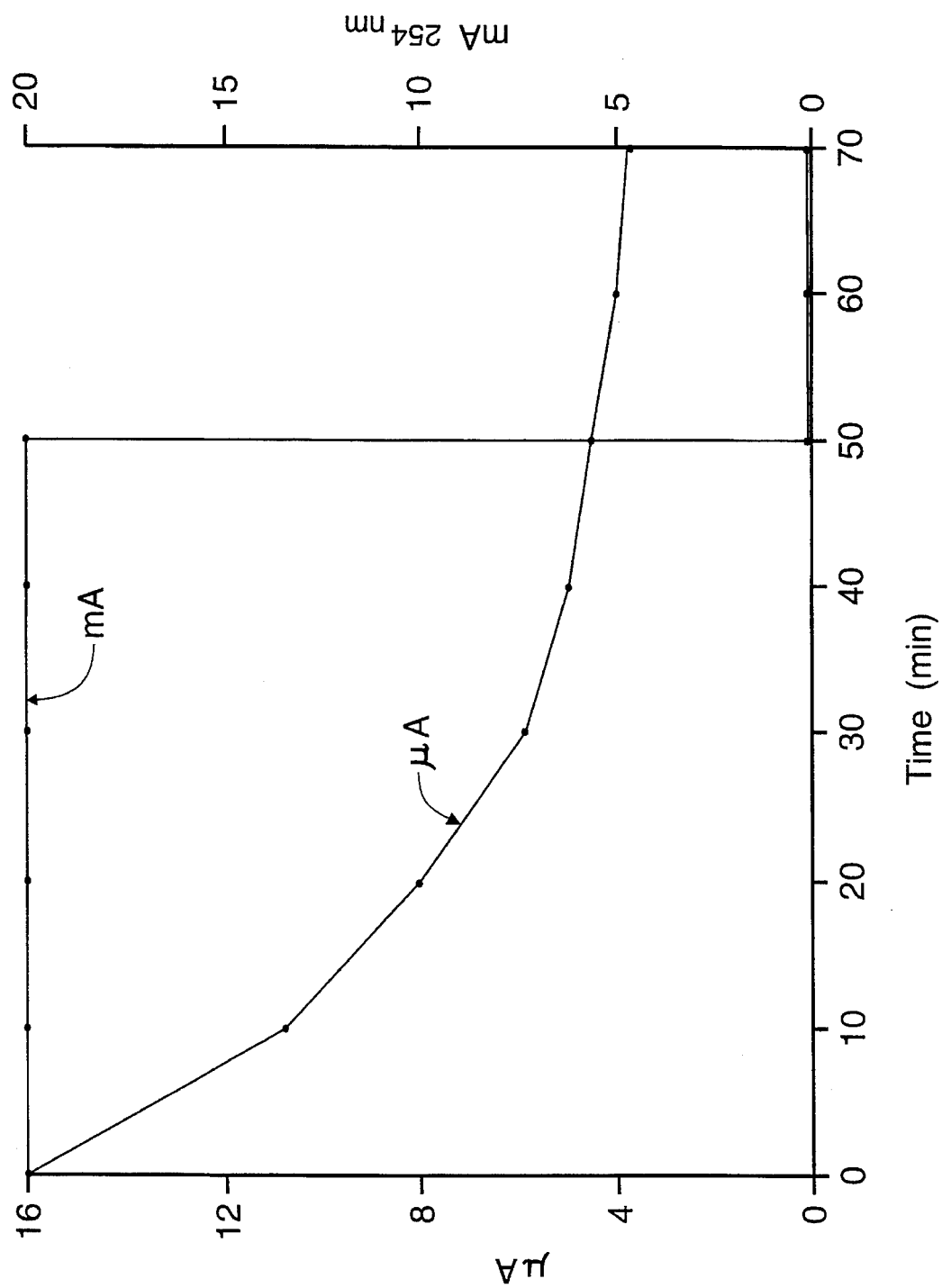

In the present invention, a method is also proposed for eliminating unwanted, toxic, free acrylamide monomers. Upon polymerizing either a 'chemical' or a 'physical' gel, as much as 10–15% unreacted monomers remain in the liquid phase. Such monomers can react with proteins and modify their residues (e.g., —SH groups, terminal —$NH_2$, 5-amino groups of Lys, the imidazole moiety of His); in addition, they will strongly absorb at 260 nm, a typical wavelength for nucleic acid detection. While in an open gel slab they could be removed by washing (although no guarantee of complete elimination can be given), no simple diffusion process exists in a closed system (such as in a capillary filling). In such cases (as well as in cases where complete acrylamide elimination is needed, such as isoelectric membranes and preparative electrophoresis processes) a chemical scavenging method has been found which consists of electrphoretically driving driving sulfhydryl compoundsthrough the matrix (or viscous solution) at mildly alkaline pH values, e.g., pH 8.5–9, and letting them react till complete addition of the —SH group to the double bond of acrylamide. The adduct thus formed can then be driven electrophoretically out of the separation column. An example of such a scavenging method is given in FIG. 6. It is seen that, as the rear boundary of the acrylamide-Cys adduct emerges from the capillary, the background absorbance drops sharply to zero. Identical results are obtained with cysteine, thioglycolic acid and other sulfhydryl-compounds. This scavenging method can also be applied in the absence of an electric field, e.g. in all gel matrices which can be removed from their container.

Laterally aggregated polyacrylamide matrices

Figure 7:
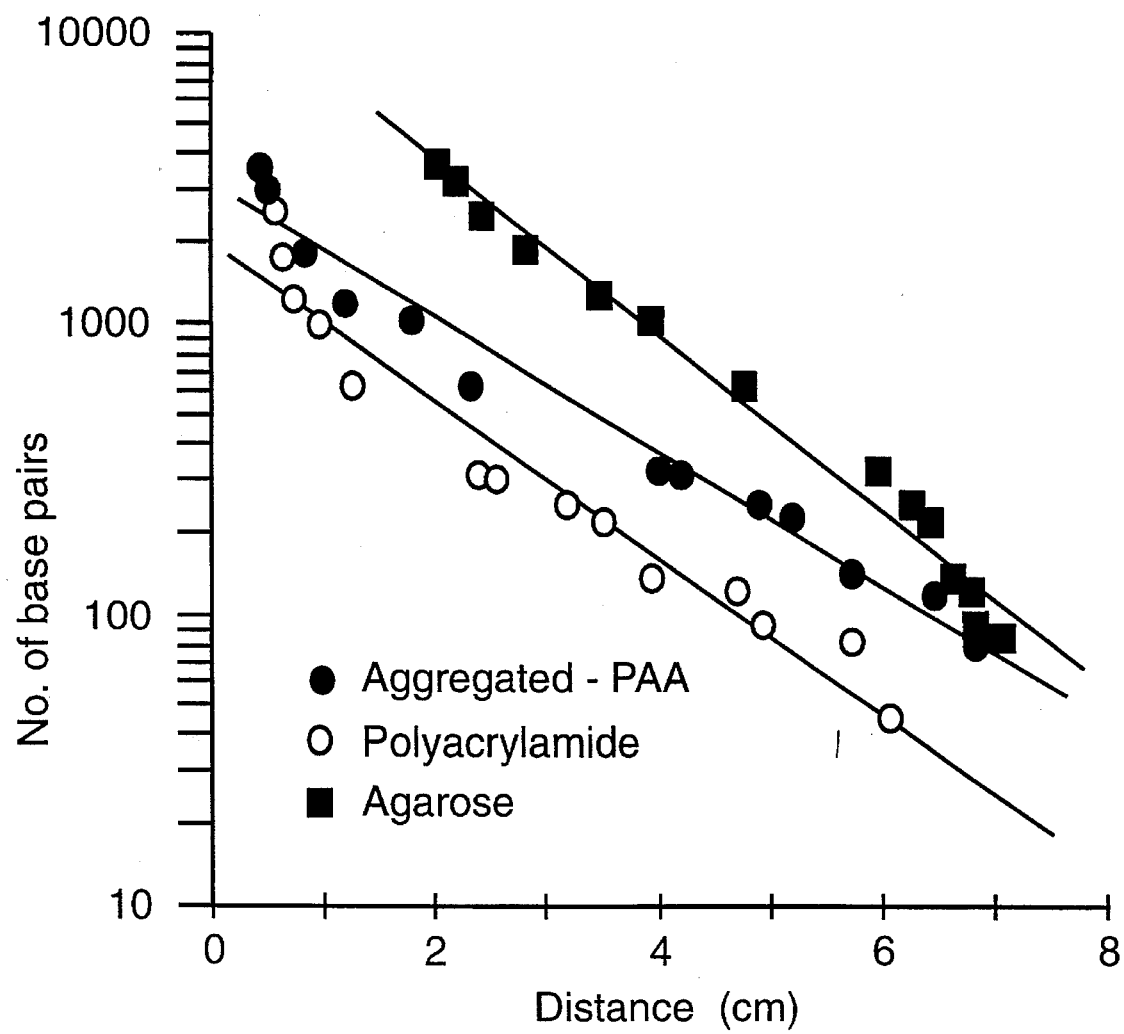

A well known method for increasing the porosity of polyacrylamides consists in utilizing a high % C (=cross-linker), while maintaining constant the % T (total amount of mono- and bi-functional monomers). It has been demonstrated that, at high % C (>50%), polyacrylamide matrices become extremely porous (up to 500 nm pore diameter) [A. Bianchi Bosisio, C. Loeherlein, R. S. Snyder and P. G. Righetti, J. Chromatogr. 189 (1980) 317–330], which would render them quite interesting for fractionating large $M_r$ DNA fragments and viral particles. Unfortunately, such matrices are useless in electrokinetic processes, since, at high % C, they become hydrophobic, collapse in the gravitational field and exude water. We describe here a new method for rendering polyacrylamide matrices highly porous: it consists of adding, to the polymerizing monomer mixture, special agents which force the nascent chains to aggregate laterally. Such agents are in general hydrophilic polymers (e.g., polyethylene glycol, polyvinylpyrrolidone, hydroxymethyl cellulose) which, when added at a given concentration to the monomer mixture, force the chains to agglomerate together, thus forming a gel network having fibres of a much larger diameter than that of a regular polyacrylamide gel (the latter believed to be ca. 0.5 nm): automatically, this is accompanied by an increase in porosity. Contrary to highly cross-linked gels, laterally-aggregated gels do not exude their hydration water and do not tend to collapse. In general, such gels are polymerized in presence of variable amounts of laterally aggregating agents, typically from 0.5 to 10%. If the polymerization is not conducted in the presence of a constant amount of such agents, but of a gradient thereof (e.g., polyethylene glycol, PEG, with an average molecular mass of 10,000 Da), it is possible to obtain a porosity gradient in the gel, which allows for optimum separation over a large spectrum of molecular sizes. Such laterally-aggregated gels have been utilized for separating DNA fragments, ranging in size from a few hundred to a few thousand base pairs (bp). These experiments have been conducted in parallel with both conventional polyacrylamides (4% T) and agarose gels (1.2%). The resolving power is expressed in a semi-log graph, by plotting the log (bp) (abscissa) vs. migration distance. The slope of the regression lines gives the useful interval for fractionation in any gel type. In the example of FIG. 7, it is seen that in a conventional polyacrylamide gel the useful fractionation range spins from ca. 50 to ca. 1000 bp, whereas a 1.2% agarose gel covers a $M_r$ range from ca. 500 to 10,000 bp. The two lines have a quasi-parallel slope and lie at a distance of ca. one order of magnitude on the scale of molecular sizes. The same polyacrylamide gel, when polymerized in the presence of laterally-aggregating agents, cuts diagonally between the two other lines, thus covering in an optimum manner the range of molecular sizes from 200 to 4000 bp. It is thus seen that such laterally-aggregated gels can cover the 'dark' zone in between polyacrylamides and agarose, i.e. that interval of $M_r$ values where polyacrylamides sieve too much and agarose are too porous. Laterally-aggregated gels have a porosity in general higher by two orders of magnitude as compared to equivalent gels polymerized under standard conditions. Thus, a conventional 6% T, 4% C gel has an average pore diameter of ca. 5–6 nm; conversely, the same gel, polymerized in the presence of 10% PEG-10K, exhibits an average porosity of ca. 500 nm, as seen at the scanning electron macroscope. Such highly porous gels are useful not only as matrices for support in techniques requiring minimal sieving, such as isoelectric focusing and immobilized pH gradients, but also as membranes in, e.g., electrophoretic or chromatographic processes based on membrane equipment. One such a process, isoelectric focusing of proteins in multicompartment electrolyzers with isoelectric membranes (based on the concept of immobilized pH gradients) has been recently described (Righetti, P. G., Wenisch, E. and Faupel, M., J. Chromatogr. 475, 1989, 293–309). One of the rate-limiting factors in this instrument is the porosity of the membranes, which considerably slows down protein migration from chamber to chamber. When these membranes were made with 'laterally aggregated' gels, protein migration was incremented by ca. one order of magnitude.

Photopolymerization of polyacrylamide matrices

It has been recently demonstrated [P. G. Righetti, M. Chiari, E. Casale and C. Chiesa, Applied Theor. Electr. 1 (1989) 115–121; G. Cossu, M. G. Pirastru, M. Satta, M. Chiari, C. Chiesa, and P. G. Righetti, J. Chromatogr. 475 (1989) 283–292] that in matrices polymerized with the standard redox couple (persulfate and TEMED) all buffers containing amino groups (from primary to tertiary; e.g., the carrier ampholyte buffers for isoelectric focusing, P. G. Righetti, Isoelectric Focusing: Theory, Methodology and Applications, Elsevier, Amsterdam, 1983, or the Immobiline buffer for immobilized pH gradients, P. G. Righetti, Immobilized pH Gradients: Theory and Methodology, Elsevier, Amsterdam, 1990) are oxidized with production of N-oxides. Even when discharging the excess persulfate to the anode prior to the electrophoretic migration, the N-oxides thus produced remain in the gel and can oxidize —SH groups of proteins during the electrophoretic run, thus producing artefacts. An alternative to chemical polymerization is photopolymerization, e.g. in presence of riboflavin (or riboflavin-5'-phosphate) and light. This process has been extensively studied in the past, but it was discarded due to its low yield (<60% conversion of the monomers into the polymer matrix, vs. a >90% conversion in persulfate polymerization) (P. G. Righetti, C. Gelfi and A. Bianchi-Bosisio, Electrophoresis 2, 1981, 291–295). In the present invention, optimum photopolymerization conditions are described for the first time, which allow >98% conversion (even greater than with persulfate). They consist of:

a) utilizing light sources with a greater power (>100 W) and with a more pronounced ultraviolet spectrum (UV-A) (in the past, standard conditions described were with 16-W-neon bulbs);

b) and/or augmenting the photopolymerization temperature to >50° C., especially when operating with low-wattage bulbs.

Figure 8:
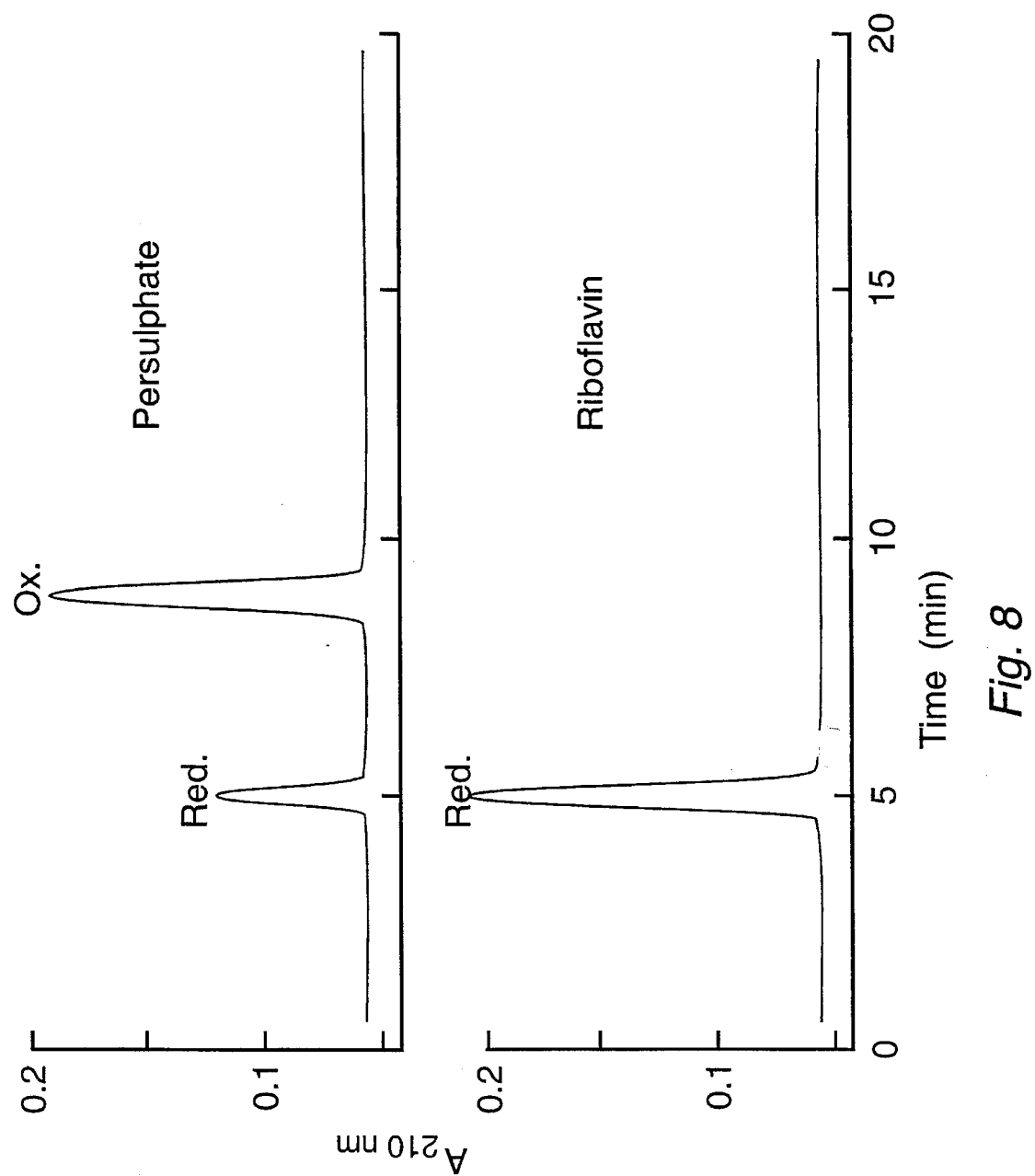
Figure 9:
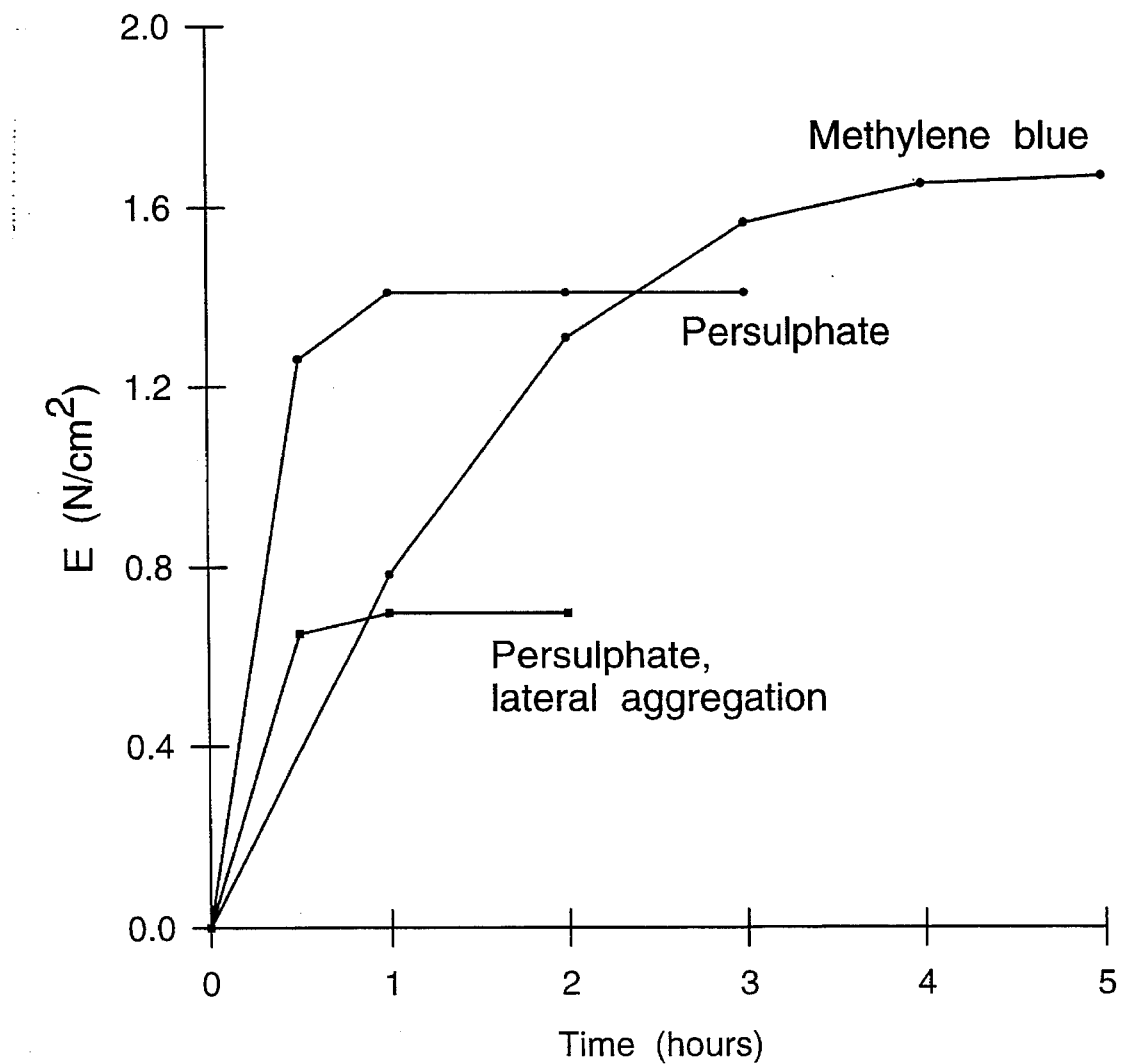

The new conditions described in the present invention render photopolymerization a more valid process than the redox chemistry utilized up to present times. In photopolymerization there is another great added advantage: the total lack of oxidizing power during the polymerization process. FIG. 8 gives an example of such a phenomen: a tertiary amine (an analogue of the pK 7.0 Immobiline, without the acrylic double bond) has been incubated either with the puersulfate/TEMED couple or with riboflavin and light, under standard conditions (1 h at 50° C. in both cases). After reaction, the tertiary amine has been analyzed by CZE: as shown in FIG. 8A, the peak of the pK 7.0 compound generates a second peak (attributed, after NMR analysis, to the N-oxide). This N-oxide species is completely absent in the electropherogram of the photopolymerized product. In addition to photopolymerization with riboflavin, we report here a most efficient system, consisting of photopolymerizing with methylene blue (e.g., 50 µM) in presence of sodium toluenesulfinate and diphenyuliodonium chloride (typically 1 mM and 50 µM, respectively): this system has the same advantages of riboflavin polymerization (i.e., lack of oxidizing power) but in addition produces gels with better visco-elastic properties than in the case of persulfate-polymerization (see FIG. 9).

Some, non-limitative examples on the preparation of the novel matrices according to the present invention are reported below.

EXAMPLE NO. 1

Synthesis of N-(2-hydroxyethoxy)ethyl-acrylamide. The above monomer is obtained as follows: to 120 mL of $CH_2Cl_2$ are added 20 mL (0.278 mol) of aminoethoxyethanol and 27.6 mL (0.198 mol) or triethylamine. This solution is added dropwise with 16 mL (0.198 mol) of acryloyl chloride (at ca. 0° C.) and stirring is continued for about 2 hours at room temperature. After filtering the precipitated salts, the organic phase is washed (twice, 100 mL each time) with pH 5.5 phosphate buffer in presence of NaCl. After drying over $Na_2SO_4$, the last residues of organic solvent are evaporated in a rotavapor. The product is analyzed by TLC in $CHCl_3/CH_3OH$ (7:3 and then 9:1) as eluent. Yield: ca. 8 g. The product is purified on a silica column, eluted first with $CH_2Cl_2/CH_3OH$ (95:5) and then with $CH_2Cl_2/CH_3OH$ (9:1).

According to the same process, N-(2-hydroxyethoxy)ethyl-methacrylamide and N,N-di(2-hydroxyethoxy)ethyl-acrylamide are obtained.

EXAMPLE NO. 2

A N(-2-hydroxyethoxy)ethyl-acrylamide solution is prepared (4% T, with 4% of a cross-linker, such as N,N'-methylene bisacrylamide of DHEBA, or bisacryloyl piperazine or similar compounds) in 40 mM Tris-acetate buffer, 20 mM Na-acetate and 2 mM EDTA, pH 8.4. The solution is degassed with a water pump for 10 min and then added with TEMED (1 µL per mL of gelling solution). The solution is divided into 2 aliquots, one is rendered 0.2% in PEG-10K, the other 2% in PEG-10K. Ten mL of each solution are transferred to a 2-chamber gradient mixer and added with 10 mL of 4% ammonium persulfate per mL of gelling solution (under stirring). The two valves are opened and the electrophoresis cassette is filled with 20 mL of a linear gradient (from 0.2 to 2% PEG-10K) at constant monomer concentration. After 1 hour polymerization at room temperature, the electrophoretic separation of DNA fragments is performed as described in the legend to FIG. 5. The polyacrylamide control is polymerized in the same way, but in the absence of PEG-10K. Analogous results are obtained when using N(-2-hydroxyethoxy)ethyl-acrylamide or acrylamide-N,N-di-ethoxy ethanol. Matrices of this kind (either at constant or variable porosity) can be washed, dryed and utilized later on, after reswelling with the desired additives (e.g., plain solvent, 8M urea, ionic, non-ionic or zwitterionic detergents, carrier ampholytes and the like, or mixture thereof).

EXAMPLE NO. 3

One proceeds as in the example 2, but in the absence of PEG-10K. The matrices obtained with our novel class of N-mono and di-substituted acrylamides, even without the larger pore size due to the presence of PEG-10K, are found extremely resistant to alkaline hydrolysis and excellent for long-term storage.

EXAMPLE NO. 4

The monomers described in the present invention can be photopolymerized, as in the example No. 2 (either in the presence or absence of PEG-10K), by adding 0.4 µL/mL of TEMED as accelerator and riboflavin (or riboflavin-5'-phosphate) at a final concentration of $2.32 \times 10-5$ mMol/ml of gelling solution. Photopolymerization continues for 1 hour at 10 cm distance from a 105-W UV-A lamp at room temperature or in front of a 16-W neon lamp at 70° C. Alternatively, photopolymerization is obtained in the presence of 50 µM methylene blue, 1 mM sodium toluenesulfinate and 50 µM diphenyliodonium chloride. Also in this case the gel can be immediately utilized, or else washed, dried and stored for future use, by reswelling in presence of the desired additives, as described in example No. 2.

LEGENDS

FIG. 1

Kinetics of hydrolysis of different acrylamide monomers. Hydrolysis has been performed in 0.1N NaOH at 70° C. for the times indicated. The amounts were assessed by harvesting triplicates at each point, neutralizing and injecting in a CZE instrument (Beckman P/ACE). Conditions: 100 mM borate-NaOH buffer, pH 9.0, 15 kV, 86 µA at 25° C. Uncoated fused silica capillary of 50 cm length, 75 µm inner diameter. Peak integration with the Beckman system Gold (mandelic acid has been used as internal standard). Abbreviations: Acr: acrylamide; DMA: N,N-dimethyl acrylamide; ACM: acryloyl morpholine; dd-Tris: di-deoxy trisacryl; Tris-A: trisacryl. Note that Tris-A (and similarly all other types of acrylamide sugars) exhibit zero-order degradation kinetics, whereas most other mono- and di-substituted monomers (including unsubstituted acrylamide) exhibit first order kinetics. In comparison, the degradation rate is much less pronounced for the novel class of N-substituted monomers here proposed, such as AAEE (acrylamido-N-ethoxy ethanol).

FIG. 2

Degradation kinetics of the monomers into the polymeric gel. The different monomers were polymerized (by emulsion polymerization) as beads, subjected to hydrolysis in 0.1N NaOH, 70° C. for the times indicated, and then analyzed for hydrolytic products. Hydrolysis was assessed in the beads by titrating free acrylic acid residues, produced by hydrolysis of the amide bond, by frontal analysis. Note the extreme stability of the novel monomers proposed in the present invention, such as acrylamido-N-ethoxy ethanol.

FIG. 3

Check for hydrolysis of different matrices. A poly-acrylamide (PAA) gel and a poly-acrylamido-N-ethoxy ethanol (AAEE) gels were cast onto a glass coated with Bind-Silane and then subjected to hydrolysis in 0.1M NaOH for 20 min at 70° C. (curves 1). After extensive washing and drying, the gels were re-swollen in 2% pH 3–10 carrier ampholytes and subjected to isoelectric focusing (2 hrs at 1500 V, 4° C.) The gels were sliced along the electrode distance and the pH measured after equilibration in 300 µL of 10 mM NaCl. Note the flattening and marked acidification of the pH gradient in the PAA gels (with an inflection point at pH 4.7, the pK value of acrylic acid), compared to the extreme stability of the poly(AAEE) matrix. Polyacrylamide gels appear to be also quite unstable upon simple overnight incubation in 100 mM Tri-borate buffer, pH 8.5 (curves 2).

FIG. 4

Hydrophobicity scale of 7 acrylamide monomers. It has been obtained by partitioning in water/n-octanol at room temperature and quantifying the concentration in the two phases by CZE. Conditions: 100 mM borate-NaOH buffer, pH 9.0, 15 kV, 86 µA at 25° C. Fused silica capillary of 50 cm length, 75 µm inner diameter. Peak integration with the Beckman system Gold (the pK 9.3 Immobiline was used as internal standard). Abbreviations: TrisA: trisacryl; AEE: acrylamido-N-ethoxy ethanol; Acr: acrylamide; MMA: mono methyl acrylamide; DMA: N,N-dimethyl acrylamide; ACM: acryloyl morpholine; DD-Tris: di-deoxy trisacryl.

FIG. 5

Separation of DNA restriction fragments in viscous solutions of linear poly(AAEE). A 10% solution of AAEE was polymerized in the capillary in the absence of cross-linker. After eliminating unreacted monomers (see FIG. 6), the capillary was equilibrated electrophoretically in 100 mM tri-borate buffer, pH 8.5 and 2 mM EDTA. A solution of 0.25 µg/mL of DNA restriction fragments was introduced in the capillary by electrophoresis (4000 V, 7 µA, 3 sec) and separated at 5000 V (8.8 µA) in a 100 µm (inner diameter) fused-silica capillary in a Waters Quanta 4000 instrument (detection at 258 nm). The fragments are (from left to right); 125, 564, 831, 947, 1375, 1584, 1904, 2027, 3530, 4268, 4973, 5148 and 22226 base pairs (bp).

FIG. 6

Scavenging of free, unreacted acrylamide by sulfhydryl compounds. After polymerizing the gel (or viscous solution) a 200 mM Tris-borate, pH 9.0, buffer, containing 100 mM cysteine, is driven electrophoretically in the capillary towards the anode for 10 h at 3 kV. After this treatment, the Cys-acrylamide adduct is driven out by replacing the anoidic vessel solution with 200 mM Tris-borate, pH 9.0 and continuing the electrophoresis for 4 h at 5 kV. Note that, after 50 min, a sharp rear boundary of reaction products emerges and the absorbance (mA, at 254 nm) drops to zero. At this point, the current (µA) tends to level off, as the capillary is now filled with the new buffer solution. Prior to analysis, the capillary is electrophoretically equilibrated in the desired running buffer (e.g., for DNA analysis, 100 mM Tris-borate, pH 8.5).

FIG. 7.

Comparison among electrophoresis of DNA fragments (double-stranded) in lateral-aggregation gels (4% T), standard polyacrylamide gels (4% T) and in agarose gels (1.2%). A series of DNA fragments (from 123 to 6000 bp) are made to migrate in the two different polyacrylamide gels at 50 V for 3 hours and in the agarose gel at 60 V for 1 hour and 30 min (total sample load: 1.67 µg DNA). All gels had the following dimensions: 7×7 cm with 1.2 mm thickness. The migration distances from the sample loading well to the center of each zone (as revealed by ethidium bromide staining) are plotted against the log of molecular mass (bp) of the fragments. Migration buffer: 40 mM Tris-acetate, 20 mM Na-acetate and 2 mM EDTA, pH 8.4. The laterally aggregated gel has been obtained by eluting from a 2-chamber gradient mixer a solution of constant monomer concentration (4% T, 4% C), in presence of a linear gradient of aggregating agent (from 0.2 to 5% PEG-10K).

FIG. 8

Formation of N-oxides during chemical polymerization. A 10 mM solution of an analogous of the pK 7.0 Immobiline (morpholinopropylacetamide) is incubated (50° C., 1 h) either in presence of 1.2% persulfate and 1 mM TEMED or in presence of riboflavin (2 mM) and light (105 W UV-A lamp). After incubation, the products are analyzed by capillary zone electrophoresis (Waters Quanta 4000) in a 50 mM phosphate buffer, pH 7.0 (15 kV, 86 µA, detection at 254 nm). Upper panel: persulfate incubation; lower panel: riboflavin incubation. Note the absence of the N-oxide peak in the lower panel, clearly visible in the upper electropherogram. The same results (absence of oxidizing power) are obtained with methylene blue polymerization.

FIG. 9

Dependence of the elastic modulus (E, in Newtons/cm$^2$) from the polymerization time in the case of methlene blue polymerization (upper), persulfate (intermediate) and persulfate in the presence of laterally-aggregating agents (lower) curves. In the last case the gel was chemically polymerized in the presence of 2% polyethylene glycol 10,000 Da. Note that, although a plateau is reached at a slower rate, the best elastic properties are exhibited in the case of photopolymerization.

We claim:

1. A poly-(N-substituted)acrylamide matrix in the form of a gel, to be used in electrokinetic or chromatographic methods, obtained by polymerization of monomers having the formula (I):

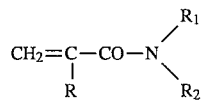

in which R represents hydrogen or $CH_3$, while $R_1$ and $R_2$, independently, represent hydrogen or a group having the formula $—\{(CH_2)_n—O—(CH_2)_n—O\}_m—H$, where n=2 or 3 and m=1–5, with the proviso that one of $R_1$ and $R_2$ is different from hydrogen, or by copolymerization of the same monomers with other acrylamides or methacrylamides, said polymerization or copolymerization conducted in the presence of a hydrophilic polymer producing lateral chain aggregation.

2. A poly-(N-substituted)acrylamide matrix according to claim 1, obtained by polymerization of N-(2-hydroxyethoxy)ethyl-acrylamide, N-(2-hydroxyethoxy)ethyl-methacrylamide, N,N-di(2-hydroxyethoxy)ethyl-acrylamide, or N,N-di(2-hydroxyethoxy)ethyl-methacrylamide, or by copolymerization thereof with N,N-dimethyl-acrylamide or N,N-dimethyl-methacrylamide.

3. A poly-(N-substituted)acrylamide matrix according to claim 1 wherein said hydrophilic polymer is a member selected from the group consisting of polyethylene glycol and polyvinylpyrrolidone.

4. A poly-(N-substituted)acrylamide matrix according to claim 1, obtained by photopolymerization or photocopolymerization of monomers having formula (I).

5. A poly-(N-substituted)acrylamide matrix according to claim 4, wherein said photopolymerization or photocopolymerization is carried out in the presence of riboflavin with a UV-A lamp of wattage >50-W at a temperature >50° C.

6. A poly-(N-substituted)acrylamide matrix according to claim 4, wherein said photopolymerization or photocopolymerization is carried out in the presence of methylene blue, and sodium toluenesulfinate and diphenyliodonium chloride.

7. A poly-(N-substituted)acrylamide matrix according to claim 1, wherein said matrix is treated with one or more chemical scavengers to add to and thereby eliminate any double bonds of unreacted acrylamide.

8. A method for performing electrokinetic separation of a mixture of proteins, nucleic acid fragments, or both, said method comprising subjecting said mixture to electrokinetic separation conditions in a matrix obtained by polymerization of monomers having the formula:

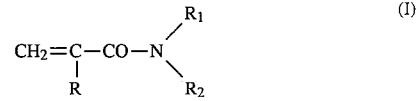

in which R represents hydrogen or $CH_3$, while $R_1$ and $R_2$, independently, represent hydrogen or a group having the formula $—\{(CH_2)_n—O—(CH_2)_n—O\}_m—H$, where n=2 or 3 and m=1–5, with the proviso that one of $R_1$ and $R_2$ is different from hydrogen, or by copolymerization of the same monomers with other acrylamides or methacrylamides, said polymerization or copolymerization conducted in the presence of a hydrophilic polymer producing lateral chain aggregation.

9. A capillary having an inner wall coated with a monomer having the formula:

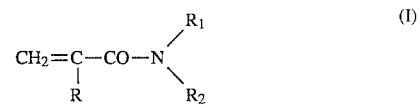

in which R represents hydrogen or $CH_3$, while $R_1$ and $R_2$, independently, represent hydrogen or a group having the formula $—\{(CH_2)_n—O—(CH_2)_n—O\}_m—H$, where n=2 or 3 and m=1–5, with the proviso that one of $R_1$ and $R_2$ is different from hydrogen, said monomer linked to said inner wall through bifunctional agents forming either —Si—O—Si— bonds or direct —Si—C≡ bonds said polymerization or copolymerization conducted in the presence of a hydrophilic polymer producing lateral chain aggregation.

10. A method for determining protein molecular sizes in a mixture of proteins by sodium dodecyl sulfate electrophoresis, said method comprising subjecting said mixture to electrophoresis in a matrix obtained by polymerization of monomers having the formula:

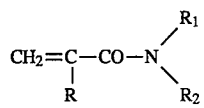

in which R represents hydrogen or $CH_3$, while $R_1$ and $R_2$, independently, represent hydrogen or a group having the formula $—\{(CH_2)_n—O—(CH_2)_n—O\}_m—H$, where n=2 or 3 and m=1–5, with the proviso that one of $R_1$ and $R_2$ is different from hydrogen, or by copolymerization of the same monomers with other acrylamides or methacrylamides said polymerization or copolymerization conducted in the presence of a hydrophilic polymer producing lateral chain aggregation.

11. A method for performing electrophoresis of a mixture of proteins, nucleic acid fragments, or both, said method comprising subjecting said mixture of electrophoretic separation conditions in a matrix obtained by polymerization of monomers having the formula:

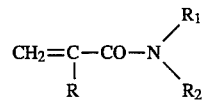

in which R represents hydrogen or $CH_3$, while $R_1$ and $R_2$, independently, represent hydrogen or a group having the formula $—\{(CH_2)_n—O—(CH_2)_n—O\}_m—H$, where n=2 or 3 and m=1–5, with the proviso that one of $R_1$ and $R_2$ is different from hydrogen, or by copolymerization of the same monomers with other acrylamides or methacrylamides said polymerization or copolymerization conducted in the presence of a hydrophilic polymer producing lateral chain aggregation.

12. A method for purifying proteins in protein preparations containing at least one of pyrogens, nucleic acid fragments and viral particles, said method comprising isoelectrically focusing said proteins in isoelectric buffering membranes in multicompartment electrolyzers to remove any pyrogens, nucleic acid fragments or viral particles present in said protein preparations, said isoelectric buffering membranes comprised of a matrix obtained by polymerization of monomers having the formula:

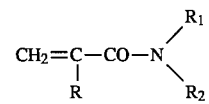

in which R represents hydrogen or $CH_3$, while $R_1$ and $R_2$, independently, represent hydrogen or a group having the formula $—\{(CH_2)_n—O—(CH_2)_n—O\}_m—H$, where n=2 or 3 and m=1–5, with the proviso that one of $R_1$ and $R_2$ is different from hydrogen, or by copolymerization of the same monomers with other acrylamides or methacrylamides said polymerization or copolymerization conducted in the presence of a hydrophilic polymer producing lateral chain aggregation.

13. A method for preparing gel slabs for long-term storage prior to use in an electrokinetic separation, said gels having been obtained by polymerization of monomers having the formula:

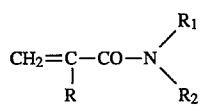

in which R represents hydrogen or $CH_3$, while $R_1$ and $R_2$, independently, represent hydrogen or a group having the formula $—\{(CH_2)_n—O—(CH_2)_n—O\}_m—H$, where n=2 or 3 and m=1–5, with the proviso that one of $R_1$ and $R_2$ is different from hydrogen, or by copolymerization of the same monomers with other acrylamides or methacrylamides, said method comprising either impregnating said slabs with a nonaqueous solvent or washing and drying said slabs said polymerization or copolymerization conducted in the presence of a hydrophilic polymer producing lateral chain aggregation.

14. Chromatographic beads comprised of a polymer obtained by polymerization of monomers having the formula:

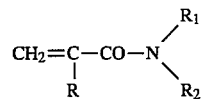

in which R represents hydrogen or $CH_3$, while $R_1$ and $R_2$, independently, represent hydrogen or a group having the formula $—\{(CH_2)_n—O—(CH_2)_n—O\}—H$, where n=2 or 3 and m=1–5, with the proviso that one of $R_1$ and $R_2$ is different from hydrogen, or by copolymerization of the same monomers with other acrylamides or methacrylamides, said polymerization or copolymerization conducted in the presence of a hydrophilic polymer producing lateral chain aggregation.

15. Chromatographic beads comprised of a core of plastic or glass coated with a polymer obtained by polymerization of monomers having the formula:

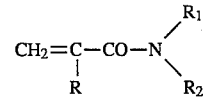

in which R represents hydrogen or $CH_3$, while $R_1$ and $R_2$, independently, represent hydrogen or a group having the formula $—\{(CH_2)_n—O—(CH_2)_n—O\}_m—H$, where n=2 or 3 and m=1–5, with the proviso that one of $R_1$ and $R_2$ is different from hydrogen, or by copolymerization of the same monomers with other acrylamides or methacrylamides, said polymerization or copolymerization conducted in the presence of a hydrophilic polymer producing lateral chain aggregation.

* * * * *